United States Patent [19]

Engstrom

[11] 4,231,425
[45] Nov. 4, 1980

[54] EXTRACORPOREAL CIRCUIT BLOOD HEAT EXCHANGER

[76] Inventor: William R. Engstrom, 17 Willow St., Belmont, Mass. 02178

[21] Appl. No.: 881,392

[22] Filed: Feb. 27, 1978

[51] Int. Cl.³ .......................... F28D 7/02; F28F 9/22
[52] U.S. Cl. .................................. 165/156; 165/159; 165/163; 165/164; 165/169
[58] Field of Search ................. 165/169, 46, 159, 163, 165/154, 156, 164

[56] References Cited

U.S. PATENT DOCUMENTS

| | | | |
|---|---|---|---|
| 1,804,624 | 5/1931 | King | 165/156 |
| 2,446,054 | 7/1948 | McCullough | 165/159 |
| 3,468,371 | 9/1969 | Menze | 165/156 |
| 4,019,020 | 4/1977 | Bilbee et al. | 165/46 |

FOREIGN PATENT DOCUMENTS

| | | | |
|---|---|---|---|
| 2441664 | 3/1976 | Fed. Rep. of Germany | 165/169 |
| 1255437 | 12/1961 | France | 165/163 |
| 2237156 | 2/1975 | France | 165/169 |

*Primary Examiner*—Sheldon Richter
*Attorney, Agent, or Firm*—Morse, Altman, Oates & Bello

[57] ABSTRACT

A heat exchanger is provided for use in a blood handling system whereby the blood may be selectively heated or cooled, as required by the nature and stage of the operation. The heat exchanger, in the preferred embodiment, is in the form of a cylindrical housing having walls defining a helical path for the flow of blood through the exchanger and about the axis of the housing. The heat exchanging medium, typically water, flows separately through a conduit in the housing, the walls of which at least partially define the helical blood conduit for heating or cooling the blood flowing therethrough. The heat exchanger is characterized by a controlled route for the blood so as to uniformly expose the blood to the same type of heating or cooling and without creating dead spots in the blood flow. A long path of blood flow is provided in a small package with a highly efficient thermal transfer.

6 Claims, 13 Drawing Figures

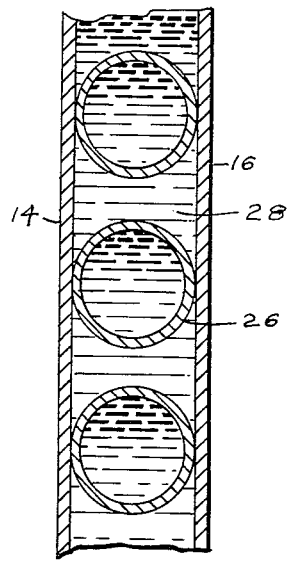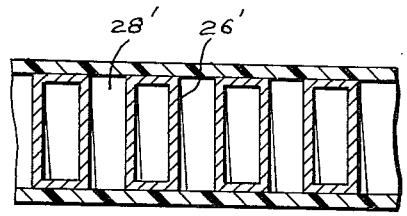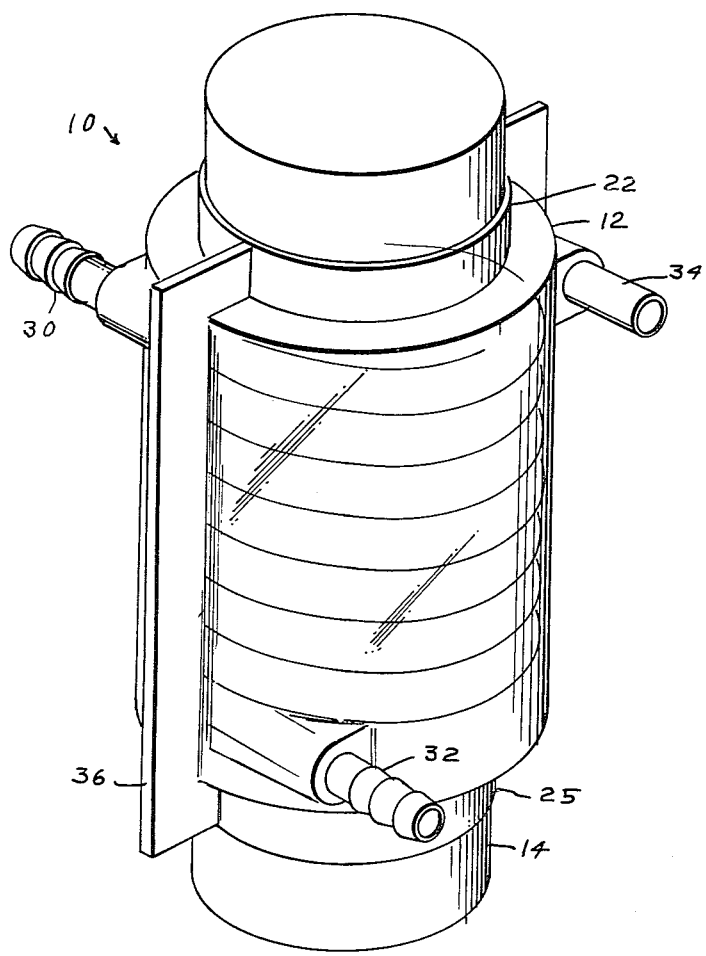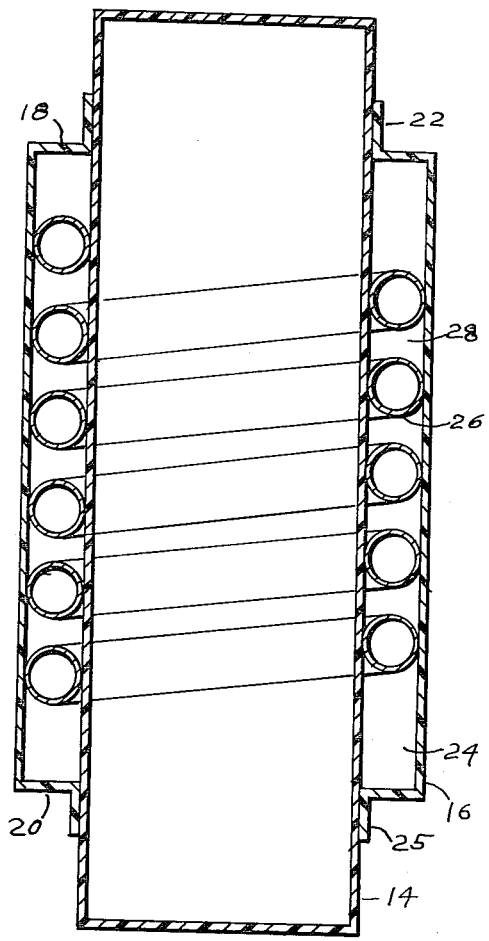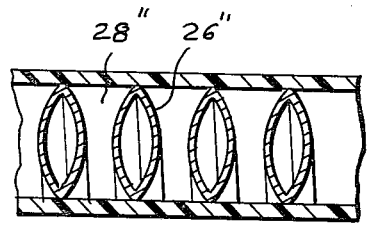

EXTRACORPOREAL CIRCUIT BLOOD HEAT EXCHANGER

BACKGROUND OF THE INVENTION

1. Field of the Invention

This invention relates generally to heat exchangers and more particularly is directed towards a new and improved heat exchanger for use in an extracorporeal blood handling system such as a blood oxygenator, or the like.

2. Description of the Prior Art

In many major surgical operations, particularly those involving open-heart surgery, it is the practice to connect the patient to a life support system by means of which the patient's blood is oxygenated artificially in an extracorporeal blood circuit and returned. During the course of the operation, control over the blood temperature is of great importance. In some instances it is desirable to maintain the blood at normal body temperature whereas in other instances it is desirable to chill the blood, particularly during coronary perfusion. Heat exchangers heretofore available for controlling blood temperature have not been satisfactory for a number of reasons, one of which is the poor control over the blood flow through the exchanger which prevents uniform thermal transfer. Typical prior art heat exchangers do not guide the blood into a controlled path or define a positive route for the blood, with the result that some of the blood flowing through the heat exchanger tends to follow a high flow route while other portions of the blood tend to be trapped in low flow zones or dead spots. Such a condition results in non-uniform thermal transfer so that all of the blood is not uniformly heated or cooled.

Accordingly, it is an object of the present invention to provide improvements in heat exchangers for extracorporeal blood handling systems. Another object of this invention is to provide a blood heat exchanger of high efficiency, long flow path and compact size. Still another object of this invention is to provide a simple, positive acting and highly efficient heat exchanger for extracorporeal blood circuits, which, in addition to providing heat exchanging functions, may also serve as a venous reservoir, a filter, an oxygenator, as well as a cardiotomy reservoir.

SUMMARY OF THE INVENTION

This invention features a heat exchanger for use in an extracorporeal blood handling system, comprising walls forming a generally cylindrical housing and defining a helical passage for blood extending from one end of the housing to the other. The walls also define a second flow path for a heat exchange medium, such as water, separately through the housing with the walls thereof common to at least some of the walls defining the blood path whereby the blood, which will be in a well formed slug, will pass through the heat exchanger without any portions thereof being trapped in dead spots and without further damage to the blood.

BRIEF DESCRIPTION OF THE DRAWINGS

FIG. 1 is a view in perspective of a heat exchanger made according to the invention,
FIG. 2 is a sectional view in side elevation thereof,
FIG. 3 is a detailed sectional view thereof,
FIG. 4 is another detailed sectional view thereof,
FIGS. 5 and 6 are views similar to FIG. 3 but showing modifications thereof.

DETAILED DESCRIPTION OF THE PREFERRED EMBODIMENTS

Figure 11:
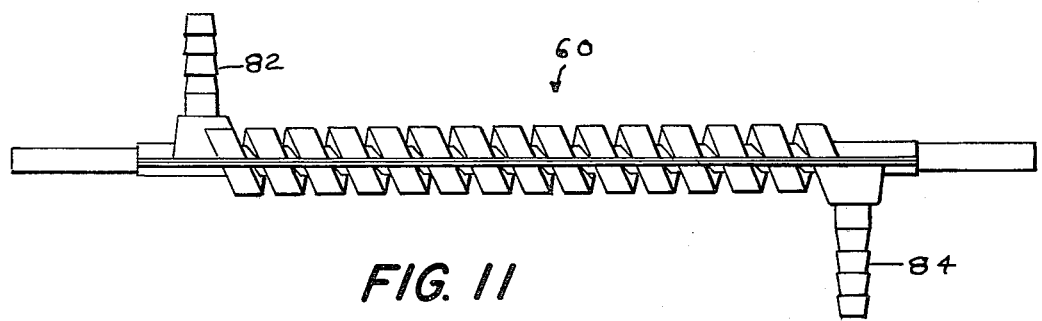
FIG. 11 is a top plan view thereof.

The heat exchanger is generally indicated by the reference character 10 and is organized about a housing 12 comprised of a tubular cylindrical inner wall 14 and a cylindrical outer wall 16 mounted in spaced parallel coaxial relation to the inner wall 14 by means of top and bottom annular walls 18 and 20 and annular flanges 22 and 25. The walls 14 and 16 define a spaced annular chamber 24 in which is mounted a length of tubing 26 which is helically wound in the chamber 24 and extends from one end to the other thereof in a series of evenly spaced convolutions. The outside diameter of the tubing 26 generally corresponds with the width of the annular chamber 24 so that the several convolutions of the tubing 26 define a helical blood passage 28 between adjacent convolutions of the tubing extending from one end of the chamber 24 to the other. Insofar as the tubing fits snuggly between the walls 14 and 16, there is no leakage between adjacent convolutions in the blood passage 28 which might disturb the desired path of the flow of blood.

The heat exchanger can be made relatively small, typically on the order of perhaps 4" in diameter and a length of perhaps 5" to 6". The dimensions are not critical but may be changed as required. In practice, the housing is fabricated from a clear, transparent material and for this purpose polycarbonate, rigid vinyl or an acrylic may be used to advantage. It is desirable to use a clear plastic material in order that the attendant may observe the development of any bubbles of air in the blood flowing through the chamber and eliminate the same by tapping on the housing.

The tubing 26 is connected to a suitable source of heat exchange medium, typically water, by means of connections 30, one at each end of the helical coil, extending out through the housing. Details of a suitable tubing connection 30 are shown in FIG. 4. Preferably the tubing 26 is fabricated of a material having good thermal conductance characteristics, and for this purpose nickel-coated copper has been found to be satisfactory insofar as it is easily formed into a coil and does not react with the blood which is flowing through the chamber 24 along the helical passage 28. The blood is introduced to the chamber 24 through an inlet connector 32 and discharged through a similar connector 34 at the top of the unit. Preferably the connectors 32 and 34 are molded as part of the housing and preferably are formed with barbs to provide a tight seal with flexible tubing fitted onto the connectors for introducing and removing blood to and from the exchanger. Suitable coupling means may be provided for connecting the tubing connectors 30 to a water supply that is appropriately heated or cooled.

The housing may be fabricated as by molding or casting techniques and, in practice, the outer walls of the housing, namely the flanged wall 16, may be fabricated in two halves, as best shown in FIG. 1. Each half is semi-cylindrical and formed with mating flanges 36 which are joined to one another to form a tight seal over the tubing coil that has been assembled on the tubular cylinder section 14 in the center. The flange 36 merges with the annular flanges 22 and 25 to form a continuous seal through the housing.

The helical blood passage 28, as best shown in FIG. 3, forms the blood into a controlled slug which moves steadily through the heat exchanger without the formation of differential flow paths in which some portions of the blood flow at velocities different from other portions thereof. Because of the controlled nature of the blood flow, no dead spots develop and all of the blood passing through the heat exchanger will be uniformly heated or cooled, as required. Further, the blood will flow with a certain amount of turbulence which is desirable to ensure good thermal transfer from the tubing to the blood in the helical blood passage. It has been found that the closer the spacing between adjacent convolutions of the tubing 26, the more turbulence will be introduced in the blood flow, although with a reduction in flow rate. The flow rate is increased by increasing the space between adjacent coil convolutions but with a commensurate decrease in turbulence. By forming the tubing into a helix and thereby producing a helical blood flow bath, a relatively small, compact heat exchanger provides a relatively long flow path for the blood, which is desirable for optimizing thermal transfer. A blood flow path of 6' to 7' is obtainable in a heat exchanger which may be less than a foot in length.

The length of the flow path is determined by the length of the tubing, the number of convolutions, and the spacing between adjacent convolutions.

The cross-sectional shape of the slug of blood in the passage 28 of FIG. 3 is somewhat H-shaped by virtue of the straight walls 14 and 16 and the circular cross-sectional tubing 26. In order to reduce the angle at the corners between the tubing and the walls in which blood might get trapped, tubings of different cross-sectional configurations may be used, as suggested in FIGS. 5 and 6. In FIG. 5, tubing 26' of rectangular cross-section is employed to form blood passages 28' of similar cross-section. In FIG. 6, tubing 26'' of elliptical cross-section is employed to form blood paths 28'' of a cross-section somewhat modified from that of the FIG. 3 embodiment.

Figure 8:
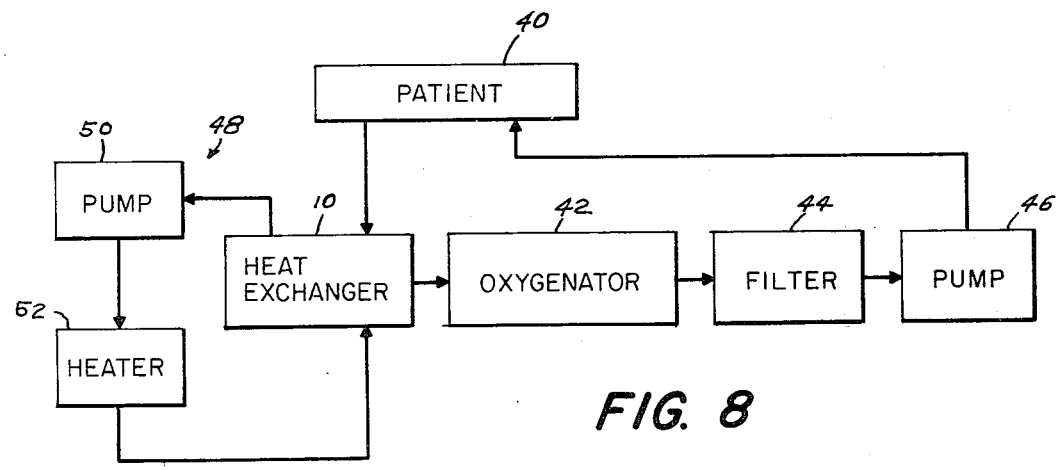
FIG. 8 is a block diagram showing a heat exchanger made according to the invention installed in a blood handling system.

Referring now to FIG. 8 of the drawings, there is illustrated in block diagram a typical extracorporeal blood circuit utilizing a heat exchanger. In FIG. 8 the patient is indicated by reference character 40, with the heat exchanger 10 connected to the venous side of an oxygenator 42 and to the patient 40. Venous blood from the patient passes through the heat exchanger before passing through the oxygenator 42. From the oxygenator 42 the blood is filtered at 44 and delivered by a pump 46 back to the patient. The temperature of the heat exchanger is maintained by a loop 48 comprised of a pump 50 and a heater 52, the loop circulating heated water through the heat exchanger 10. Appropriate control accessories (not shown) may be provided, such as temperature sensing devices to measure the temperature of the blood entering and leaving the heat exchanger, and control regulators for maintaining control over the temperature and flow of water passing through the heat exchanger. If the blood passing through the heat exchanger is to be cooled, then an appropriate cooling device would be used in place of the heater 52. In practice, the control components of the loop 48 should be adjusted so that the temperature of the water entering the heat exchanger is not more than 10° to 12° higher than the temperature of the blood going into the heat exchanger.

Preferably the heat exchanger 10 is installed on the venous side of the oxygenator in order to bring gas out of solution. It has been found that if the blood is oxygenated prior to heating, any entrained air/oxygen bubbles in the blood enlarge and can result in permanent brain damage to the patient. By heating the blood prior to oxygenation, any such entrained air bubbles are removed.

Figure 7:
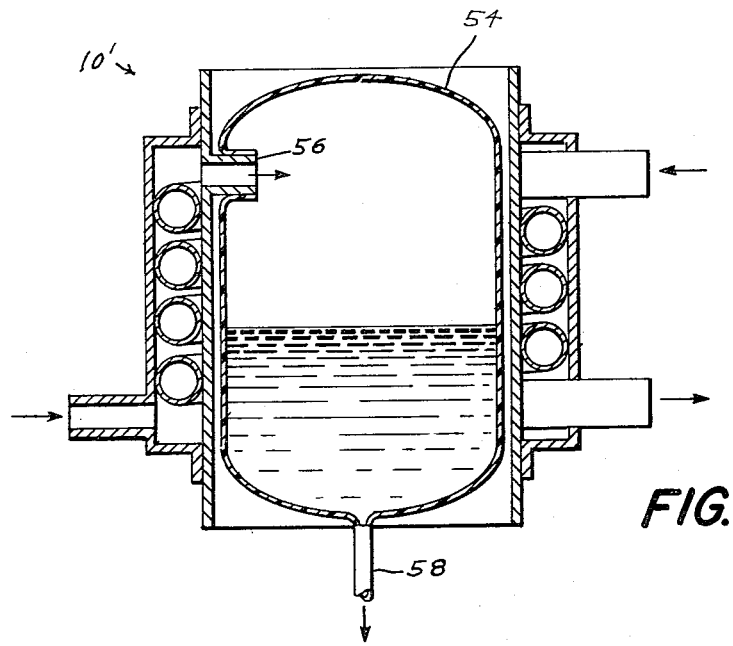
FIG. 7 is a sectional view in side elevation showing a modified heat exchanger.
Figure 9:
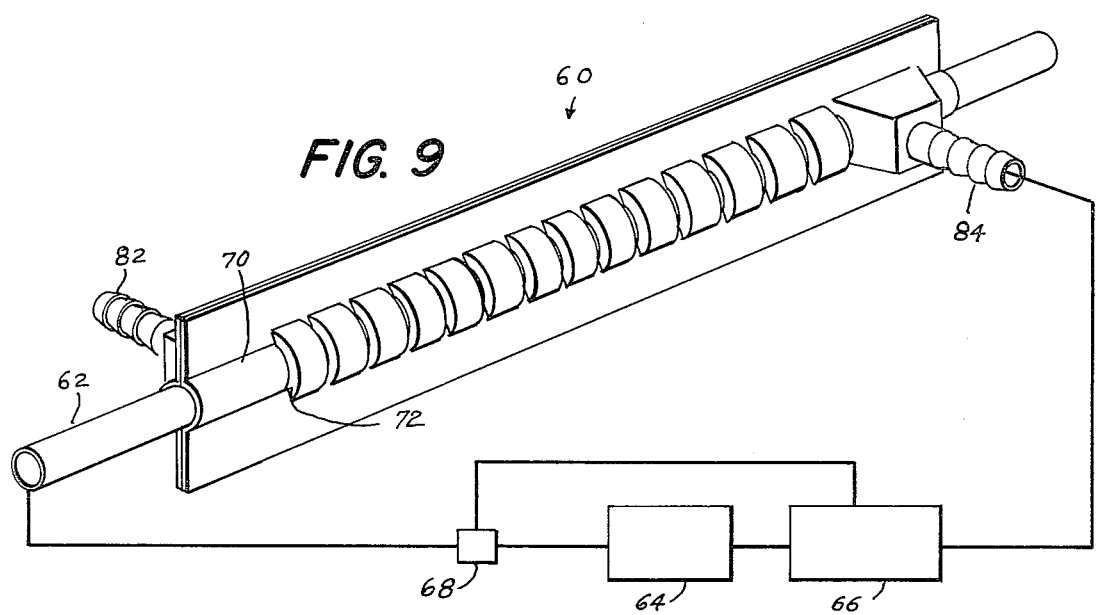
FIG. 9 is a view in perspective, somewhat schematic, showing another modification of the heat exchanger.
Figure 10:
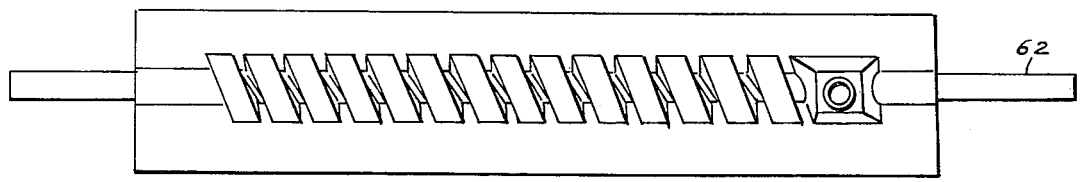
FIG. 10 is a view in side elevation thereof.
Figure 12:
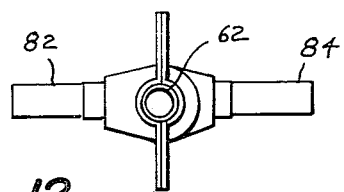
FIG. 12 is an end elevation thereof.
Figure 13:
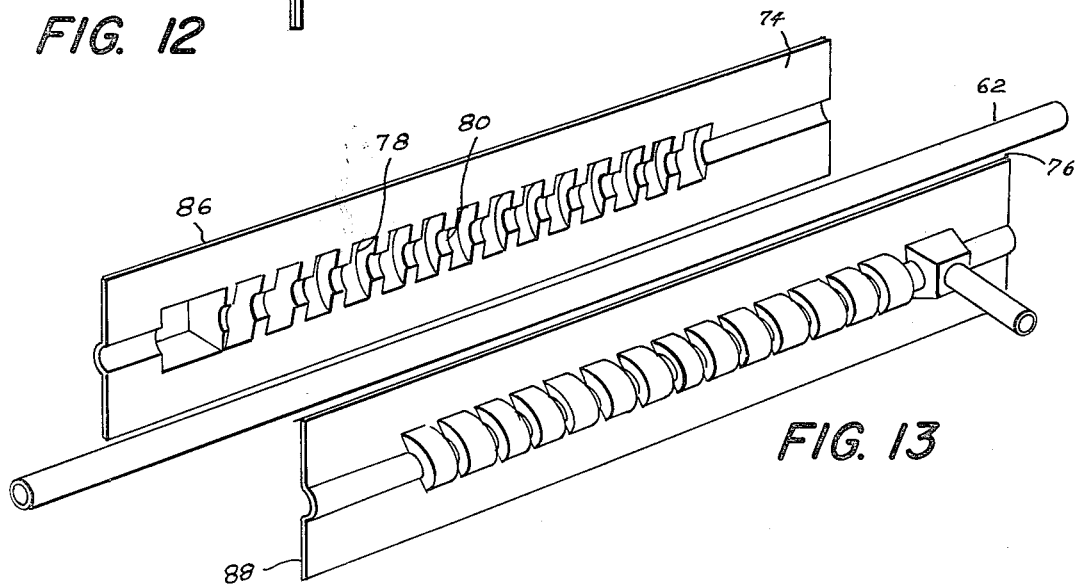
FIG. 13 is an exploded view in perspective of the modified heat exchanger.

Referring now to FIG. 7 of the drawings, there is illustrated a modification of the invention, and in this embodiment a heat exchanger 10' is provided in a configuration similar to that of the principal embodiment, with the exception that a flexible plastic bag 54 is mounted in the center of the unit and the blood outlet is by means of an inwardly extending neck 56 which connects to the bag as shown. The bag provides a flexible reservoir for venous blood and serves to collect the blood without introducing air thereto. The blood can be stored in the bag or delivered by means of a conduit 58 to another stage in the circuit. In place of the bag 54 other functional components may be mounted in the center of the tubular heat exchanger. Such, for example, a filter or a capillary membrane could be provided to act as an oxygenator. The assembly may also be provided with a container for use as a cardiotomy reservoir, if desired.

Referring now to FIGS. 9 through 13, there is illustrated another modification of the invention and, in this embodiment, there is provided a heat exchanger 60 which is particularly useful for coronary perfusion procedures. The heat exchanger 60 is organized about a single, straight tube 62 through which heating or cooling liquid is pumped in a straight flow path. For this purpose, a pump 64 is provided and either a heating or cooling unit 66, operated by means of appropriate temperature sensing and controlling device 68, is connected to the pump.

Bonded to the tube 62, which preferably is of a good heat-conductive material, such as nickel-coated copper, is a housing 70 which forms a helical passage 72 about the outer surface of the tube 62. The passage is formed by means of a pair of housing halves 74 and 76, each half having a mating series of internal, evenly spaced semi-helical recesses 78 and semi-cylindrical recesses 80 which, when the halves are fitted over the tube 62, form the continuous helical passage 72 along the outer surface of the tube. The recesses 80 fit snuggly against the surface of the tube while the recesses 78 form the helical blood flow path. Inlet and outlet fittings 82 and 84 are molded into opposite ends of the housing through which the blood is fed in and out of the heat exchanger. Each housing half is formed with a relatively wide flange 86 and 88 appropriately designed to fit snuggly against one another and over the tube, the flanges being bonded to one another to prevent leakage. Similarly, the recesses 80 are tightly fitted against the tube to prevent leakage between adjacent convolutions.

In the heat exchanger of this embodiment, it is desirable that the housing be fabricated from a clear, transparent plastic material in order that the operator may observe the flow of blood and the occurrence of any air bubbles.

While the invention has been described with particular reference to the illustrated embodiments, numerous modifications thereto will appear to those skilled in the art.

Having thus described the invention, what I claim and desire to obtain by Letters Patent of the United States is:

1. A heat exchanger for use in an extracorporeal blood circuit, or the like, comprising
    (a) a housing of a clear, transparent material,
    (b) said housing including walls forming a portion of a helical passage for the flow of blood therethrough,
    (c) a tubular conduit mounted to and passing through said housing for the flow of a heat exchange medium therethrough,
    (d) the exterior of said conduit forming another portion of said helical passage whereby blood flowing through said helical passage will be in direct contact with said conduit,
    (e) said housing including a cylindrical inner wall and a cylindrical outer wall spaced from the inner wall to define an annular chamber therebetween,
    (f) said conduit being in the form of a helix and mounted in said chamber, each convolution of said conduit being in contact with the inner and outer walls and spaced from adjacent convolutions to define said helical passage, and,
    (g) blood receiving means disposed within said inner wall and connected to the discharge end of said helical blood passage,
    (h) said inner wall being tubular and said outer wall being comprised of a pair of cooperating semi-cylindrical shell sections having end flanges and joined to one another and to said inner wall.

2. A heat exchanger, according to claim 1, wherein the cross-sectional shape and dimension of said passage is substantially constant over the major portion thereof.

3. A heat exchanger, according to claim 1, wherein one shell section is formed with inlet and outlet connections for said helical blood passage and said other shell section is formed with sealed openings through which the ends of said conduit extend.

4. A heat exchanger, according to claim 1, wherein said tubular conduit is circular in cross-section.

5. A heat exchanger, according to claim 1, wherein said tubular conduit is rectangular in cross-section.

6. A heat exchanger, according to claim 1, wherein said tubular conduit is elliptical in cross-section.

* * * * *